United States Patent
Korb

(10) Patent No.: US 11,989,738 B2
(45) Date of Patent: *May 21, 2024

(54) SYSTEMS AND METHODS FOR INTERDEPENDENT IDENTITY BASED CREDENTIAL COLLECTION VALIDATION

(71) Applicant: Accreditrust Technologies, LLC, Alexandria, VA (US)

(72) Inventor: Eric R. Korb, Watchung, NJ (US)

(73) Assignee: Accreditrust Technologies, LLC, Alexandria, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/170,830

(22) Filed: Feb. 17, 2023

(65) Prior Publication Data
US 2023/0252488 A1 Aug. 10, 2023

Related U.S. Application Data

(63) Continuation of application No. 14/883,285, filed on Oct. 14, 2015, now Pat. No. 11,587,096.

(51) Int. Cl.
*G06Q 30/01* (2023.01)
*G06F 21/10* (2013.01)
*G06Q 30/018* (2023.01)
*G16H 20/10* (2018.01)

(52) U.S. Cl.
CPC ........... *G06Q 30/018* (2013.01); *G06F 21/10* (2013.01); *G16H 20/10* (2018.01)

(58) Field of Classification Search
CPC .................................................. G06Q 30/018
See application file for complete search history.

(56) References Cited

U.S. PATENT DOCUMENTS

| | | | |
|---|---|---|---|
| 4,716,593 A | 12/1987 | Hirai | |
| 7,209,889 B1* | 4/2007 | Whitfield | G06Q 20/02 705/72 |
| 7,318,155 B2* | 1/2008 | Yellepeddy | H04L 9/321 713/176 |
| 7,457,950 B1* | 11/2008 | Brickell | G06F 21/33 705/317 |
| 7,617,970 B2 | 11/2009 | Carr | |
| 8,406,480 B2 | 3/2013 | Grigsby | |
| 8,517,254 B1 | 8/2013 | Cipriano | |
| 8,620,676 B2 | 12/2013 | Geller | |
| 8,667,561 B2 | 3/2014 | Wang | |
| 8,713,650 B2 | 4/2014 | Piliouras | |

(Continued)

OTHER PUBLICATIONS

International Search Report and Written Opinion corresponding to PCT/US2016/057110 dated Jan. 19, 2017, 6 pages.

(Continued)

*Primary Examiner* — Patrick McAtee
*Assistant Examiner* — Nakia Leffall-Allen
(74) *Attorney, Agent, or Firm* — Sheppard Mullin Richter & Hampton LLP

(57) ABSTRACT

A system for digitally verifying credential sets and its method of use are provided. A credentials set is made up of a number of credentials, each linked to a particular Entity. If all of the credentials are validated and verified, then the credentials' status identifier will be set to a value. If the various status identifiers meet a predetermined value, the set will be verified and digitally signed.

23 Claims, 2 Drawing Sheets

(56) References Cited

U.S. PATENT DOCUMENTS

| | | |
|---|---|---|
| 9,032,213 B2 | 5/2015 | Mashima |
| 10,362,033 B1 | 7/2019 | Saylor |
| 2005/0138367 A1 | 6/2005 | Paganetti |
| 2006/0129817 A1* | 6/2006 | Borneman ............. H04L 67/53 |
| | | 713/170 |
| 2007/0185814 A1* | 8/2007 | Boccon-Gibod ..... H04L 9/3242 |
| | | 705/51 |
| 2008/0256609 A1 | 10/2008 | Bodepudi |
| 2010/0325441 A1 | 12/2010 | Laurie |
| 2013/0191898 A1 | 7/2013 | Kraft |
| 2013/0275753 A1 | 10/2013 | Correa |
| 2014/0181927 A1 | 6/2014 | Sarkissian |
| 2015/0077228 A1 | 3/2015 | Dua |
| 2015/0095999 A1* | 4/2015 | Toth ..................... H04L 9/3263 |
| | | 726/6 |

OTHER PUBLICATIONS

White, Ron, "How Computers Work", Seventh Edition, (p. 4), Que Publishing, Oct. 15, 2003, 23 pages.

* cited by examiner

SYSTEMS AND METHODS FOR INTERDEPENDENT IDENTITY BASED CREDENTIAL COLLECTION VALIDATION

CLAIM OF PRIORITY

This application is a continuation of U.S. patent application Ser. No. 14/883,285, entitled "SYSTEM AND METHODS FOR INTERDEPENDENT IDENTITY BASED CREDENTIAL COLLECTION VALIDATION," filed Oct. 14, 2015, which is hereby incorporated by reference in its entirety.

FIELD OF THE EMBODIMENTS

This invention relates to systems and methods for Interdependent Credential Verification.

BACKGROUND OF THE EMBODIMENTS

Today, there are over 72 million adults in the United States who hold at least 1 or more government-issued professional licenses or certificates that are required for employment or to operate a business or practice in their chosen field; in healthcare alone, there are over 18 million state-issued licenses, registrations and certifications. Additionally, there exist over 90,000 professional associations whose membership includes more than 25,000,000 professionals throughout the country. Many associations enable their members to become certified as a result of passing rigorous testing as well as demonstrating relevant industry skills and experience. Many business entities depend on the authenticity of these certifications before they will hire, engage, or appoint professionals to various positions.

Traditionally, issuing institutions ("Issuers") commit significant resources to administer (i.e. store, track, print, mail) paper-based certificates that cannot be readily verified by third parties. As such, efforts to confirm authenticity often take the form of requests from interested parties to the Issuers to verify a given certificate.

The method of the present invention is integrated by software developers of Credential processing, instructional delivery, testing, human capital management, professional networking, and other relevant areas.

Issuers that leverage the method of the present invention can dramatically reduce their staff time and costs in administering certifications. Additionally, the dynamic updating feature of the present invention, allows viewers of micro-Credentials to be 100% confident of their authenticity.

Examples of related art are described below:

Regarding art that provides for a secure identification and Credential Verification system (and methods thereof):

U.S. Pat. No. 8,517,254 discloses a method and apparatus for verifying the validity of identification cards. A card reading device reads an ID card and transmits a request to a database server. A database is queried and a reply is sent back to the card reading device indicating whether the ID is valid. The system can also log and timestamp events for future access.

U.S. Pat. No. 8,406,480 discloses a method for verifying a visual Credential such as a Credential by assigning a security level and predetermined thresholds relating to visual Credential matching the individual. A comparison module determines whether or not the unverified Credential is valid or invalid by comparing the image of the unverified Credential with known good images of valid Credentials.

United States Publication No. 2013/0275753 teaches a system for verifying Credentials comprising a plurality of Credential Verification servers both on a local and remote server.

U.S. Pat. No. 8,620,676 discloses an electronic Credential Verification system which is comprised of electronic Credential records, a database to store such Credentials, real time access to the database, verification data and storage; and automatic and continuous verification of Credentials.

Further, much of the prior art deals with fraud detection and protection.

U.S. Pat. No. 8,713,650 discloses a computer implemented system to detect fraudulent data which performs a comparison of information related to an Identity Document of a first subscriber with prior activity data corresponding to prior use of that same Identity Document, the prior activity data received from a device of a second subscriber and stored in the database.

U.S. Pat. No. 7,617,970 teaches a system that creates a computer score and depending on the computed scoring, the system determines whether or not the individual's ID Credential scoring is sufficient to verify the individual or reject an individual ID Credentials.

United States Publication No. 2013/0191898 discloses a method for facilitating the authentication and verification of a user by creating and maintaining a true online Credential (TOC). The TOC is comprised of a personally identifiable information of a user and a knowledge-based-authentication (KBA) question and response.

United States Publication No. 20110197267 teaches a system for authenticating an Identity of a user of a client device (mobile or otherwise) as part of a transaction between the client device and a server of a service provider over a communications network.

U.S. Pat. No. 4,716,593 teaches an Identity verification system based on speech rather than ID Credentials.

An understanding of Digital Credentials and the current process is necessary to understand the present invention. Exchanging Digital Credentials is generally an electronic process. The process primarily involves at least two parties: 1) An Issuer, who is responsible for issuing the Digital Credential and, 2) the Recipient, who is the Entity that is the focus of the Credential's Claim. The Issuer uses a software application to create and store a Digital Credential, which software application then notifies the Recipient of the existence of said Credential for the Recipient to store in another software application capable of curating Digital Credentials on behalf of the Recipient.

The W3C Credentials Group ("CG") has proposed a specification for describing how Issuers will create and deliver a Digital Credential to a Recipient. In this model, a software application requests Identity information from the Recipient, such as a decentralized identifier (DID), which is provided by Recipient's Identity Provider ("IdP") through a standardized web protocol especially designed to communicate Digital Credentials and DIDs called the Credential Transport Protocol ("CTP"). A web service, known as WebDHT, is designed to communicate and manage DIDs over the internet. Once the IdP authenticates the Recipient, the IdP composes and sends out an Identity Document that contains the Recipient's DID. The Issuer then creates and stores a Digital Credential that contains a reference to the Recipient's DID and notifies the Recipient of the existence of a newly issued Credential. When the Recipient claims the Digital Credential, it is sent from the Issuer's Credential storage system to the Recipient's curation system using the CTP. IdPs who support CTP usually provide a Digital Credential curation system. The W3C specification goes on to describe how to apply standardized cryptography using public/private key (PKI) encryption methods to sign a Digital Credential's meta-data. Digitally signed Credentials can be systematically verified to ensure that the meta-data has not been tampered with prior to further inspection by the Entity evaluating or consuming the Digital Credential. Using PKI encryption involves signing the Digital Credential's meta-data with a Private Key owned by the Issuer. A signed Digital Credential contains a Digital Signature value within the Digital Credential meta-data, which is verified using the corresponding Public Key derived from the Issuer's Private Key. Metaphorically speaking, the Private Key "locks the door, but can't open it"; the Public Key "opens the door but can't lock it." The Digital Signature contained in the Digital Credentials ensures that is was composed by the owner (generally the Recipient) of the Public/Private Key, and is used to verify that the meta-data contained in the Digital Credential has not been modified after it was originally signed with the Issuer's Private Key.

The following is a use case example of the above Digital Credential process methodology:

There are many types of Issuers that can exist: Two types such entities are educational institutions and healthcare providing institutions. Educational institutions will be able to provide validated Digital Credentials for people who have already earned them, or preferably, a student will take a test provided by the educational institution that has already been optimized for the system of the present invention. An example of the latter is now provided:

A student (the Recipient in this illustration) goes to an educational institution's (the Issuer) test center and sits down at a computer. The educational institution needs to acquire the Student's DID so it will be able to issue him a Digital Credential once his test results are evaluated. To do this, the educational institution's computerized testing system requests an email Credential from student's IdP, which sends an Identity Document back to the institutions testing system that contains the student's DID, a link to the student's Email Address Digital Credential, and a Digital Signature proving that the information is owned by student. The student's DID and email address (ascertained from their verified Email Address Digital Credential) are stored and associated with their submitted test answers in the institution's testing system. The testing system then evaluates the results.

Given predetermined criterion are met through the evaluation of the test results, the institution will create a Digital Credential that represents the student's achievement. The educational institution's testing system issues a Digital Credential containing Claims ("meta-data") representing the student's achievement to the student's DID and digitally signs the meta-data with the institution's Private Key. The institution's testing system then notifies the student that a Digital Credential is now ready to be claimed by him. The student logs into his IdP, and is presented with the Digital Credential by the institution's testing system. The student then claims the Digital Credential, which is then communicated and curated at the student's IdP.

Assume that after this process the student then visits a company's website to apply for a job. In order to apply for a specific job, the company requires that the student (or job applicant) have met aptitude criteria. The student has a Credential containing Claims that match the required aptitude criteria. The student wishes to offer the Digital Credential as a proof of his aptitude Claims. The company's website requests the student's DID and is directed to the student's IdP to allow him to authorize the transmission of the requested Digital Credential to the company's job application system. The job application system, upon receipt of the Digital Credential, may inspect the data integrity of the Credential by verifying the Digital Signature contained in the Digital Credential prior to storing the meta-data. After the Digital Credential is verified and stored in the job application system, the HR decision maker can be assured that the applicant meets the criteria for the job and may proceed accordingly.

The institution, student, and HR decision maker all have various incentives for participating in the system:
  Educational institutions can protect their brand and integrity of the Credentials they issue.
  Students identities are protected by use of DID and may curate their Credentials at the IdP of their choice.
  HR departments are assured they are making informed decisions based on trusted information about applicants.

As noted, the present invention is particularly suited to serve health care providers as well. In one embodiment, the present invention operates as follows:

A pharmacy needs to fulfill a prescription ("script") for a customer. The doctor who writes the script will issue a digitally signed Digital Credential with her private key, which contains the script information and the patient's DID (collectively "meta-data"). Linked to the script's Credential is another Digital Credential that contains the doctor's License, DEA Registration, National Provider Identifier (NPI), Medicare/Medicaid Enrollment Status and Exclusion/Debarment status. Prior to filling and handing over the prescription to the patient, the pharmacy needs to: ensure the doctor's credentials are valid and none of them violate a business rule; that the prescription data has not been tampered with; and prove the Identity of the person picking up the prescription is associated with or an official proxy of the DID. The pharmacy prescription system can verify all of the above using the present invention by independently validating: the prescription Digital Credential; verifying the prescriber's Digital Credential; and using the DID to get proof of the patient's Identity or proxy at the point of sale terminal.

SUMMARY OF THE EMBODIMENTS

The present invention provides for a system, comprising: a memory that stores computer-executable instructions; and a processor, communicatively coupled to said memory that facilitates execution of the computer-executable instructions which provides a Credential set comprising: at least one Credential having at least one item of legitimate information and a status identifier; wherein the system validates the format of the at least one Credential and determines whether the status identifier of the Credential satisfies a verification parameter of a Credential set, wherein said system transforms the status identifier into a set status identifier, and wherein said system uses the set status identifier to verify the Credential set, provided that the set status identifier meets a predetermined value. The system may also digitally sign the verified Credential set. The Credential and Credential Sets may be digital.

The present invention also provides for a method for Interdependent Credential Verification of a set, comprising the steps of: providing, at least one Credential, said at least one Credential comprising at least one item of legitimate information and at least one status identifier; defining, a Credential set comprising at least one Credential, comprising at least one item of information, and a status identifier;

validating, the format of said at least one Credential; determining whether the at least one Credential satisfies the parameter of the Credential set; transforming, said status identifier into a set status identifier; and verifying said Credential set, provided that said set status identifier meets a predetermined value. The method may also include digitally signing said verified Credential set.

It is an object of the present invention to create a system that allows sets of interdependent Credentials to be digitally verified.

It is an object of the present invention to maintain a database of sets of interdependent Credentials for a plurality of users involving a number of different certifications.

It is an object of the present invention to provide a clearinghouse for portable interdependent Credentials that are not tied to a single Entity.

It is an object of the present invention to simplify the verification of interdependent Credentials of a given Entity.

DESCRIPTION OF THE PREFERRED EMBODIMENTS

Figure 1:
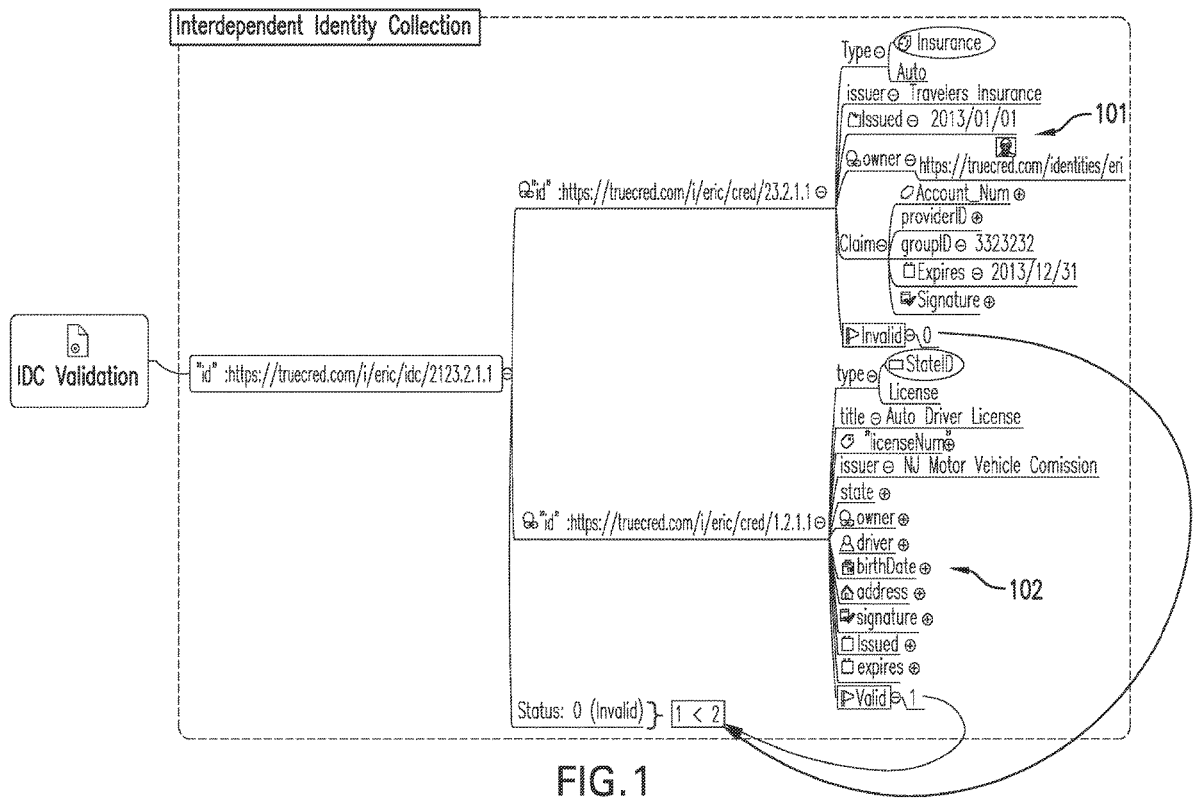
FIG. 1 shows a decision tree of an embodiment of the method of the present invention.

The preferred embodiments of the present invention will now be described with reference to the drawings. Identical elements in the various figures are identified with the same reference numerals.

Reference will now be made in detail to each embodiment of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto.

Typically, a user or users, which may be people or groups of users and/or other systems, may engage information technology systems (e.g., computers) to facilitate operation of the system and information processing. In turn, computers employ processors to process information and such processors may be referred to as central processing units ("CPU"). One form of processor is referred to as a microprocessor. CPUs use communicative circuits to pass binary encoded signals acting as instructions to enable various operations. These instructions may be operational and/or data instructions containing and/or referencing other instructions and data in various processor accessible and operable areas of memory (e.g., registers, cache memory, random access memory, etc.). Such communicative instructions may be stored and/or transmitted in batches (e.g., batches of instructions) as programs and/or data components to facilitate desired operations. These stored instruction codes, e.g., programs, may engage the CPU circuit components and other motherboard and/or system components to perform desired operations. One type of program is a computer operating system, which may be executed by CPU on a computer; the operating system enables and facilitates users to access and operate computer information technology and resources. Some resources that may be employed in information technology systems include: input and output mechanisms through which data may pass into and out of a computer; memory storage into which data may be saved; and processors by which information may be processed. These information technology systems may be used to collect data for later retrieval, analysis, and manipulation, which may be facilitated through a database program. These information technology systems provide interfaces that allow users to access and operate various system components.

In one embodiment, the present invention may be connected to and/or communicate with Entities such as, but not limited to: one or more users from user input devices; peripheral devices; an optional cryptographic processor device; and/or a communications network. For example, the present invention may be connected to and/or communicate with users operating client device(s), including, but not limited to, personal computer(s), server(s) and/or various mobile device(s) including, but not limited to, cellular telephone(s), smartphone(s) (e.g., iPhone®, Blackberry®, Android OS-based phones etc.), tablet computer(s) (e.g., Apple iPad™, HP Slate™, Motorola Xoom™, etc.), eBook reader(s) (e.g., Amazon Kindle™, Barnes and Noble's Nook™ eReader, etc.), laptop computer(s), notebook(s), netbook(s), gaming console(s) (e.g., XBOX Live™, Nintendo® DS, Sony PlayStation® Portable, etc.), portable scanner(s) and/or the like.

Networks are commonly thought to comprise the interconnection and interoperation of clients, servers, and intermediary nodes in a graph topology. It should be noted that the term "server" as used throughout this application refers generally to a computer, other device, program, or combination thereof that processes and responds to the requests of remote users across a communications network. Servers serve their information to requesting "clients." The term "client" as used herein refers generally to a computer, program, other device, user and/or combination thereof that is capable of processing and making requests and obtaining and processing any responses from servers across a communications network. A computer, other device, program, or combination thereof that facilitates, processes information and requests, and/or furthers the passage of information from a source user to a destination user is commonly referred to as a "node." Networks are generally thought to facilitate the transfer of information from source points to destinations. A node specifically tasked with furthering the passage of information from a source to a destination is commonly called a "router." There are many forms of networks such as Local Area Networks (LANs), Pico networks, Wide Area Networks (WANs), Wireless Networks (WLANs), etc. For example, the Internet is generally accepted as being an interconnection of a multitude of networks whereby remote clients and servers may access and interoperate with one another.

The present invention may be based on computer systems that may comprise, but are not limited to, components such as: a computer systemization connected to memory.

Computer Systemization

A computer systemization may comprise a clock, central processing unit ("CPU(s)" and/or "processor(s)" (these terms are used interchangeable throughout the disclosure unless noted to the contrary)), a memory (e.g., a read only memory (ROM), a random access memory (RAM), etc.), and/or an interface bus, and most frequently, although not necessarily, are all interconnected and/or communicating through a system bus on one or more (mother)board(s) having conductive and/or otherwise transportive circuit pathways through which instructions (e.g., binary encoded signals) may travel to effect communications, operations, storage, etc. Optionally, the computer systemization may be connected to an internal power source; e.g., optionally the power source may be internal. Optionally, a cryptographic processor and/or transceivers (e.g., ICs) may be connected to the system bus. In another embodiment, the cryptographic processor and/or transceivers may be connected as either internal and/or external peripheral devices via the interface bus I/O. In turn, the transceivers may be connected to antenna(s), thereby effectuating wireless transmission and reception of various communication and/or sensor protocols; for example the antenna(s) may connect to: a Texas Instruments WiLink WL1283 transceiver chip (e.g., providing 802.11n, Bluetooth 3.0, FM, global positioning system (GPS) (thereby allowing the controller of the present invention to determine its location)); Broadcom BCM4329FKUBG transceiver chip (e.g., providing 802.11n, Bluetooth 2.1+EDR, FM, etc.); a Broadcom BCM4750IUB8 receiver chip (e.g., GPS); an Infineon Technologies X-Gold 618-PMB9800 (e.g., providing 2G/3G HSDPA/HSUPA communications); and/or the like. The system clock typically has a crystal oscillator and generates a base signal through the computer systemization's circuit pathways. The clock is typically coupled to the system bus and various clock multipliers that will increase or decrease the base operating frequency for other components interconnected in the computer systemization. The clock and various components in a computer systemization drive signals embodying information throughout the system. Such transmission and reception of instructions embodying information throughout a computer systemization may be commonly referred to as communications. These communicative instructions may further be transmitted, received, and the cause of return and/or reply communications beyond the instant computer systemization to: communications networks, input devices, other computer systemizations, peripheral devices, and/or the like. Of course, any of the above components may be connected directly to one another, connected to the CPU, and/or organized in numerous variations employed as exemplified by various computer systems.

The CPU comprises at least one high-speed data processor adequate to execute program components for executing user and/or system-generated requests. Often, the processors themselves will incorporate various specialized processing units, such as, but not limited to: integrated system (bus) controllers, memory management control units, floating point units, and even specialized processing sub-units like graphics processing units, digital signal processing units, and/or the like. Additionally, processors may include internal fast access addressable memory, and be capable of mapping and addressing memory beyond the processor itself; internal memory may include, but is not limited to: fast registers, various levels of cache memory (e.g., level 1, 2, 3, etc.), RAM, etc. The processor may access this memory through the use of a memory address space that is accessible via instruction address, which the processor can construct and decode allowing it to access a circuit path to a specific memory address space having a memory state. The CPU may be a microprocessor such as: AMD's Athlon, Duron and/or Opteron; ARM's application, embedded and secure processors; IBM and/or Motorola's DragonBall and PowerPC; IBM's and Sony's Cell processor; Intel's Celeron, Core (2) Duo, Itanium, Pentium, Xeon, and/or XScale; and/or the like processor(s). The CPU interacts with memory through instruction passing through conductive and/or transportive conduits (e.g., (printed) electronic and/or optic circuits) to execute stored instructions (i.e., program code) according to conventional data processing techniques. Such instruction passing facilitates communication within the present invention and beyond through various interfaces. Should processing requirements dictate a greater amount speed and/or capacity, distributed processors (e.g., Distributed embodiments of the present invention), mainframe, multi-core, parallel, and/or super-computer architectures may similarly be employed. Alternatively, should deployment requirements dictate greater portability, smaller Personal Digital Assistants (PDAs) may be employed.

Depending on the particular implementation, features of the present invention may be achieved by implementing a microcontroller such as CAST's R8051XC2 microcontroller; Intel's MCS 51 (i.e., 8051 microcontroller); and/or the like. Also, to implement certain features of the various embodiments, some feature implementations may rely on embedded components, such as: Application-Specific Integrated Circuit ("ASIC"), Digital Signal Processing ("DSP"), Field Programmable Gate Array ("FPGA"), and/or the like embedded technology. For example, any of the component collection (distributed or otherwise) and/or features of the present invention may be implemented via the microprocessor and/or via embedded components; e.g., via ASIC, coprocessor, DSP, FPGA, and/or the like. Alternately, some implementations of the present invention may be implemented with embedded components that are configured and used to achieve a variety of features or signal processing.

Depending on the particular implementation, the embedded components may include software solutions, hardware solutions, and/or some combination of both hardware/software solutions. For example, features of the present invention discussed herein may be achieved through implementing FPGAs, which are a semiconductor devices containing programmable logic components called "logic blocks", and programmable interconnects, such as the high performance FPGA Virtex series and/or the low cost Spartan series manufactured by Xilinx. Logic blocks and interconnects can be programmed by the customer or designer, after the FPGA is manufactured, to implement any of the features of the present invention. A hierarchy of programmable interconnects allow logic blocks to be interconnected as needed by the system designer/administrator of the present invention, somewhat like a one-chip programmable breadboard. An FPGA's logic blocks can be programmed to perform the function of basic logic gates such as AND, and XOR, or more complex combinational functions such as decoders or simple mathematical functions. In most FPGAs, the logic blocks also include memory elements, which may be simple flip-flops or more complete blocks of memory. In some circumstances, the present invention may be developed on regular FPGAs and then migrated into a fixed version that more resembles ASIC implementations. Alternate or coordinating implementations may migrate features of the controller of the present invention to a final ASIC instead of or in addition to FPGAs. Depending on the implementation all of the aforementioned embedded components and microprocessors may be considered the "CPU" and/or "processor" for the present invention.

Power Source

The power source may be of any standard form for powering small electronic circuit board devices such as the following power cells: alkaline, lithium hydride, lithium ion, lithium polymer, nickel cadmium, solar cells, and/or the like. Other types of AC or DC power sources may be used as well. In the case of solar cells, in one embodiment, the case provides an aperture through which the solar cell may capture photonic energy. The power cell is connected to at least one of the interconnected subsequent components of the present invention thereby providing an electric current to all subsequent components. In one example, the power source is connected to the system bus component. In an alternative embodiment, an outside power source is provided through a connection across the I/O interface. For example, a USB and/or IEEE 1394 connection carries both data and power across the connection and is therefore a suitable source of power.

Interface Adapters

Interface bus(ses) may accept, connect, and/or communicate to a number of interface adapters, conventionally although not necessarily in the form of adapter cards, such as but not limited to: input output interfaces (I/O), storage interfaces, network interfaces, and/or the like. Optionally, cryptographic processor interfaces similarly may be connected to the interface bus. The interface bus provides for the communications of interface adapters with one another as well as with other components of the computer systemization. Interface adapters are adapted for a compatible interface bus. Interface adapters conventionally connect to the interface bus via a slot architecture. Conventional slot architectures may be employed, such as, but not limited to: Accelerated Graphics Port (AGP), Card Bus, (Extended) Industry Standard Architecture ((E)ISA), Micro Channel Architecture (MCA), NuBus, Peripheral Component Interconnect (Extended) (PCI(X)), PCI Express, Personal Computer Memory Card International Association (PCMCIA), and/or the like.

Storage interfaces may accept, communicate, and/or connect to a number of storage devices such as, but not limited to: storage devices, removable disc devices, and/or the like. Storage interfaces may employ connection protocols such as, but not limited to: (Ultra) (Serial) Advanced Technology Attachment (Packet Interface) ((Ultra) (Serial) ATA(PI)), (Enhanced) Integrated Drive Electronics ((E)IDE), Institute of Electrical and Electronics Engineers (IEEE) 1394, fiber channel, Small Computer Systems Interface (SCSI), Universal Serial Bus (USB), and/or the like.

Network interfaces may accept, communicate, and/or connect to a communications network. Through a communications network, the controller of the present invention is accessible through remote clients (e.g., computers with web browsers) by users. Network interfaces may employ connection protocols such as, but not limited to: direct connect, Ethernet (thick, thin, twisted pair 10/100/1000 Base T, and/or the like), Token Ring, wireless connection such as IEEE 802.11a-x, and/or the like. Should processing requirements dictate a greater amount speed and/or capacity, distributed network controllers (e.g., Distributed embodiments of the present invention), architectures may similarly be employed to pool, load balance, and/or otherwise increase the communicative bandwidth required by the controller of the present invention. A communications network may be any one and/or the combination of the following: a direct interconnection; the Internet; a Local Area Network (LAN); a Metropolitan Area Network (MAN); an Operating Missions as Nodes on the Internet (OMNI); a secured custom connection; a Wide Area Network (WAN); a wireless network (e.g., employing protocols such as, but not limited to a Wireless Application Protocol (WAP), I-mode, and/or the like); and/or the like. A network interface may be regarded as a specialized form of an input output interface. Further, multiple network interfaces may be used to engage with various communications network types. For example, multiple network interfaces may be employed to allow for the communication over broadcast, multicast, and/or unicast networks.

Input Output interfaces (I/O) may accept, communicate, and/or connect to user input devices, peripheral devices, cryptographic processor devices, and/or the like. I/O may employ connection protocols such as, but not limited to: audio: analog, digital, monaural, RCA, stereo, and/or the like; data: Apple Desktop Bus (ADB), IEEE 1394a-b, serial, universal serial bus (USB); infrared; joystick; keyboard; midi; optical; PC AT; PS/2; parallel; radio; video interface: Apple Desktop Connector (ADC), BNC, coaxial, component, composite, digital, Digital Visual Interface (DVI), high-definition multimedia interface (HDMI), RCA, RF antennae, S-Video, VGA, and/or the like; wireless transceivers: 802.11a/b/g/n/x; Bluetooth; cellular (e.g., code division multiple access (CDMA), high speed packet access (HSPA(+)), high-speed downlink packet access (HSDPA), global system for mobile communications (GSM), long term evolution (LTE), WiMax, etc.); and/or the like. One typical output device may include a video display, which typically comprises a Cathode Ray Tube (CRT) or Liquid Crystal Display (LCD) based monitor with an interface (e.g., DVI circuitry and cable) that accepts signals from a video interface, may be used. The video interface composites information generated by a computer systemization and generates video signals based on the composited information in a video memory frame. Another output device is a television set, which accepts signals from a video interface. Typically, the video interface provides the composited video information through a video connection interface that accepts a video display interface (e.g., an RCA composite video connector accepting an RCA composite video cable; a DVI connector accepting a DVI display cable, etc.).

User input devices often are a type of peripheral device (see below) and may include: card readers, dongles, finger print readers, gloves, graphics tablets, joysticks, keyboards, microphones, mouse (mice), remote controls, retina readers, touch screens (e.g., capacitive, resistive, etc.), trackballs, trackpads, sensors (e.g., accelerometers, ambient light, GPS, gyroscopes, proximity, etc.), styluses, and/or the like.

Peripheral devices and the like may be connected and/or communicate to I/O and/or other facilities or the like such as network interfaces, storage interfaces, directly to the interface bus, system bus, the CPU, and/or the like. Peripheral devices may be external, internal and/or part of the controller of the present invention. Peripheral devices may also include, for example, an antenna, audio devices (e.g., linein, line-out, microphone input, speakers, etc.), cameras (e.g., still, video, webcam, etc.), and/or the like.

Cryptographic units such as, but not limited to, microcontrollers, processors, interfaces, and/or devices may be attached, and/or communicate with the controller of the present invention. A MC68HC16 microcontroller, manufactured by Motorola Inc., may be used for and/or within cryptographic units. The MC68HC16 microcontroller utilizes a 16-bit multiply-and-accumulate instruction in the 16 MHz configuration and requires less than one second to perform a 512-bit RSA private key operation. Cryptographic units support the authentication of communications from interacting agents, as well as allowing for anonymous transactions. Cryptographic units may also be configured as part of CPU. Equivalent microcontrollers and/or processors may also be used. Other commercially available specialized cryptographic processors include: the Broadcom's CryptoNetX and other Security Processors; nCipher's nShield, SafeNet's Luna PCI (e.g., 7100) series; Semaphore Communications' 40 MHz Roadrunner 184; Sun's Cryptographic Accelerators (e.g., Accelerator 6000 PCIe Board, Accelerator 500 Daughtercard); Via Nano Processor (e.g., L2100, L2200, U2400) line, which is capable of performing 500+MB/s of cryptographic instructions; VLSI Technology's 33 MHz 6868; and/or the like.

Memory

Generally, any mechanization and/or embodiment allowing a processor to affect the storage and/or retrieval of information is regarded as memory. However, memory is a fungible technology and resource, thus, any number of memory embodiments may be employed in lieu of or in concert with one another. It is to be understood that the controller of the present invention and/or a computer systemization may employ various forms of memory. For example, a computer systemization may be configured wherein the functionality of on-chip CPU memory (e.g., registers), RAM, ROM, and any other storage devices are provided by a paper punch tape or paper punch card mechanism; of course such an embodiment would result in an extremely slow rate of operation. In a typical configuration, memory will include ROM, RAM, and a storage device. A storage device may be any conventional computer system storage. Storage devices may include a drum; a (fixed and/or removable) magnetic disk drive; a magneto-optical drive; an optical drive (i.e., Blueray, CD ROM/RAM/Recordable (R)/ReWritable (RW), DVD R/RW, HD DVD R/RW etc.); an array of devices (e.g., Redundant Array of Independent Disks (RAID)); solid state memory devices (USB memory, solid state drives (SSD), etc.); other processor-readable storage mediums; and/or other devices of the like. Thus, a computer systemization generally requires and makes use of memory.

Component Collection

The memory may contain a collection of program and/or database components and/or data such as, but not limited to: operating system component(s) (operating system); information server component(s) (information server); user interface component(s) (user interface); Web browser component(s) (Web browser); database(s); mail server component(s); mail client component(s); cryptographic server component(s) (cryptographic server) and/or the like (i.e., collectively a component collection). These components may be stored and accessed from the storage devices and/or from storage devices accessible through an interface bus. Although non-conventional program components such as those in the component collection, typically, are stored in a local storage device, they may also be loaded and/or stored in memory such as: peripheral devices, RAM, remote storage facilities through a communications network, ROM, various forms of memory, and/or the like.

Operating System

The operating system component is an executable program component facilitating the operation of the controller of the present invention. Typically, the operating system facilitates access of I/O, network interfaces, peripheral devices, storage devices, and/or the like. The operating system may be a highly fault tolerant, scalable, and secure system such as: Apple Macintosh OS X (Server); AT&T Plan 9; Be OS; Unix and Unix-like system distributions (such as AT&T's UNIX; Berkley Software Distribution (BSD) variations such as FreeBSD, NetBSD, OpenBSD, and/or the like; Linux distributions such as Red Hat, Ubuntu, and/or the like); and/or the like operating systems. However, more limited and/or less secure operating systems also may be employed such as Apple Macintosh OS, IBM OS/2, Microsoft DOS, Microsoft Windows 2000/2003/3.1/95/98/CE/Millennium/NT/Vista/XP (Server), Palm OS, and/or the like. The operating system may be one specifically optimized to be run on a mobile computing device, such as iOS, Android, Windows Phone, Tizen, Symbian, and/or the like. An operating system may communicate to and/or with other components in a component collection, including itself, and/or the like. Most frequently, the operating system communicates with other program components, user interfaces, and/or the like. For example, the operating system may contain, communicate, generate, obtain, and/or provide program component, system, user, and/or data communications, requests, and/or responses. The operating system, once executed by the CPU, may enable the interaction with communications networks, data, I/O, peripheral devices, program components, memory, user input devices, and/or the like. The operating system may provide communications protocols that allow the controller of the present invention to communicate with other entities through a communications network. Various communication protocols may be used by the controller of the present invention as a subcarrier transport mechanism for interaction, such as, but not limited to: multicast, TCP/IP, UDP, unicast, and/or the like.

Information Server

An information server component is a stored program component that is executed by a CPU. The information server may be a conventional Internet information server such as, but not limited to Apache Software Foundation's Apache, Microsoft's Internet Information Server, and/or the like. The information server may allow for the execution of program components through facilities such as Active Server Page (ASP), ActiveX, (ANSI) (Objective-) C (++), C# and/or .NET, Common Gateway Interface (CGI) scripts, dynamic (D) hypertext markup language (HTML), FLASH, Java, JavaScript, Practical Extraction Report Language (PERL), Hypertext Pre-Processor (PHP), pipes, Python, wireless application protocol (WAP), WebObjects, and/or the like. The information server may support secure communications protocols such as, but not limited to, File Transfer Protocol (FTP); HyperText Transfer Protocol (HTTP); Secure Hypertext Transfer Protocol (HTTPS), Secure Socket Layer (SSL), messaging protocols (e.g., America Online (AOL) Instant Messenger (AIM), Application Exchange (APEX), ICQ, Internet Relay Chat (IRC), Microsoft Network (MSN) Messenger Service, Presence and Instant Messaging Protocol (PRIM), Internet Engineering Task Force's (IETF's) Session Initiation Protocol (SIP), SIP for Instant Messaging and Presence Leveraging Extensions (SIMPLE), open XML-based Extensible Messaging and Presence Protocol (XMPP) (i.e., Jabber or Open Mobile Alliance's (OMA's) Instant Messaging and Presence Service (IMPS)), Yahoo! Instant Messenger Service, and/or the like. The information server provides results in the form of Web pages to Web browsers, and allows for the manipulated generation of the Web pages through interaction with other program components. After a Domain Name System (DNS) resolution portion of an HTTP request is resolved to a particular information server, the information server resolves requests for information at specified locations on the controller of the present invention based on the remainder of the HTTP request. For example, a request such as http://123.124.125.126/myInformation.html might have the IP portion of the request "123.124.125.126" resolved by a DNS server to an information server at that IP address; that information server might in turn further parse the http request for the "/myInformation.html" portion of the request and resolve it to a location in memory containing the information "myInformation.html." Additionally, other information serving protocols may be employed across various ports, e.g., FTP communications across port, and/or the like. An information server may communicate to and/or with other components in a component collection, including itself, and/or facilities of the like. Most frequently, the information server communicates with the database of the present invention, operating systems, other program components, user interfaces, Web browsers, and/or the like.

Access to the database of the present invention may be achieved through a number of database bridge mechanisms such as through scripting languages as enumerated below (e.g., CGI) and through inter-application communication channels as enumerated below (e.g., CORBA, WebObjects, etc.). Any data requests through a Web browser are parsed through the bridge mechanism into appropriate grammars as required by the present invention. In one embodiment, the information server would provide a Web form accessible by a Web browser. Entries made into supplied fields in the Web form are tagged as having been entered into the particular fields, and parsed as such. The entered terms are then passed along with the field tags, which act to instruct the parser to generate queries directed to appropriate tables and/or fields. In one embodiment, the parser may generate queries in standard SQL by instantiating a search string with the proper join/select commands based on the tagged text entries, wherein the resulting command is provided over the bridge mechanism to the present invention as a query. Upon generating query results from the query, the results are passed over the bridge mechanism, and may be parsed for formatting and generation of a new results Web page by the bridge mechanism. Such a new results Web page is then provided to the information server, which may supply it to the requesting Web browser.

Also, an information server may contain, communicate, generate, obtain, and/or provide program component, system, user, and/or data communications, requests, and/or responses.

User Interface

Computer interfaces in some respects are similar to automobile operation interfaces. Automobile operation interface elements such as steering wheels, gearshifts, and speedometers facilitate the access, operation, and display of automobile resources, and status. Computer interaction interface elements such as check boxes, cursors, menus, scrollers, and windows (collectively and commonly referred to as widgets) similarly facilitate the access, capabilities, operation, and display of data and computer hardware and operating system resources, and status. Operation interfaces are commonly called user interfaces. Graphical user interfaces (GUIs) such as the Apple Macintosh Operating System's Aqua, IBM's OS/2, Microsoft's Windows 2000/2003/3.1/95/98/CE/Millennium/NT/XP/Vista/7 (i.e., Aero), Unix's X-Windows (e.g., which may include additional Unix graphic interface libraries and layers such as K Desktop Environment (KDE), mythTV and GNU Network Object Model Environment (GNOME)), web interface libraries (e.g., ActiveX, AJAX, (D)HTML, FLASH, Java, JavaScript, etc. interface libraries such as, but not limited to, Dojo, jQuery(UI), MooTools, Prototype, script.aculo.us, SWFObject, Yahoo! User Interface, any of which may be used and) provide a baseline and means of accessing and displaying information graphically to users.

A user interface component is a stored program component that is executed by a CPU. The user interface may be a conventional graphic user interface as provided by, with, and/or atop operating systems and/or operating environments such as already discussed. The user interface may allow for the display, execution, interaction, manipulation, and/or operation of program components and/or system facilities through textual and/or graphical facilities. The user interface provides a facility through which users may affect, interact, and/or operate a computer system. A user interface may communicate to and/or with other components in a component collection, including itself, and/or facilities of the like. Most frequently, the user interface communicates with operating systems, other program components, and/or the like. The user interface may contain, communicate, generate, obtain, and/or provide program component, system, user, and/or data communications, requests, and/or responses.

Web Browser

A Web browser component is a stored program component that is executed by a CPU. The Web browser may be a conventional hypertext viewing application such as Microsoft Internet Explorer or Netscape Navigator. Secure Web browsing may be supplied with 128 bit (or greater) encryption by way of HTTPS, SSL, and/or the like. Web browsers allowing for the execution of program components through facilities such as ActiveX, AJAX, (D)HTML, FLASH, Java, JavaScript, web browser plug-in APIs (e.g., FireFox, Safari Plug-in, and/or the like APIs), and/or the like. Web browsers and like information access tools may be integrated into PDAs, cellular telephones, and/or other mobile devices. A Web browser may communicate to and/or with other components in a component collection, including itself, and/or facilities of the like. Most frequently, the Web browser communicates with information servers, operating systems, integrated program components (e.g., plug-ins), and/or the like; e.g., it may contain, communicate, generate, obtain, and/or provide program component, system, user, and/or data communications, requests, and/or responses. Of course, in place of a Web browser and information server, a combined application may be developed to perform similar functions of both. The combined application would similarly affect the obtaining and the provision of information to users, User Agents, and/or the like from the enabled nodes of the present invention. The combined application may be nugatory on systems employing standard Web browsers.

Mail Server

A mail server component is a stored program component that is executed by a CPU. The mail server may be a conventional Internet mail server such as, but not limited to sendmail, Microsoft Exchange, and/or the like. The mail server may allow for the execution of program components through facilities such as ASP, ActiveX, (ANSI) (Objective-) C (++), C# and/or .NET, CGI scripts, Java, JavaScript, PERL, PHP, pipes, Python, WebObjects, and/or the like. The mail server may support communications protocols such as, but not limited to: Internet message access protocol (IMAP), Messaging Application Programming Interface (MAPI)/Microsoft Exchange, post office protocol (POP3), simple mail transfer protocol (SMTP), and/or the like. The mail server can route, forward, and process incoming and outgoing mail messages that have been sent, relayed and/or otherwise traversing through and/or to the present invention.

Access to the mail of the present invention may be achieved through a number of APIs offered by the individual Web server components and/or the operating system.

Also, a mail server may contain, communicate, generate, obtain, and/or provide program component, system, user, and/or data communications, requests, information, and/or responses.

Mail Client

A mail client component is a stored program component that is executed by a CPU. The mail client may be a conventional mail viewing application such as Apple Mail, Microsoft Entourage, Microsoft Outlook, Microsoft Outlook Express, Mozilla, Thunderbird, and/or the like. Mail clients may support a number of transfer protocols, such as: IMAP, Microsoft Exchange, POP3, SMTP, and/or the like. A mail client may communicate to and/or with other components in a component collection, including itself, and/or facilities of the like. Most frequently, the mail client communicates with mail servers, operating systems, other mail clients, and/or the like; e.g., it may contain, communicate, generate, obtain, and/or provide program component, system, user, and/or data communications, requests, information, and/or responses. Generally, the mail client provides a facility to compose and transmit electronic mail messages.

Cryptographic Server

A cryptographic server component is a stored program component that is executed by a CPU, cryptographic processor, cryptographic processor interface, cryptographic processor device, and/or the like. Cryptographic processor interfaces will allow for expedition of encryption and/or decryption requests by the cryptographic component; however, the cryptographic component, alternatively, may run on a conventional CPU. The cryptographic component allows for the encryption and/or decryption of provided data. The cryptographic component allows for both symmetric and asymmetric (e.g., Pretty Good Protection (PGP)) encryption and/or decryption. The cryptographic component may employ cryptographic techniques such as, but not limited to: digital certificates (e.g., X.509 authentication framework), Digital Signatures, dual signatures, enveloping, password access protection, public key management, and/or the like. The cryptographic component will facilitate numerous (encryption and/or decryption) security protocols such as, but not limited to: checksum, Data Encryption Standard (DES), Elliptical Curve Encryption (ECC), International Data Encryption Algorithm (IDEA), Message Digest 5 (MD5, which is a one way hash function), passwords, Rivest Cipher (RC5), Rijndael, RSA (which is an Internet encryption and authentication system that uses an algorithm developed in 1977 by Ron Rivest, Adi Shamir, and Leonard Adleman), Secure Hash Algorithm (SHA), Secure Socket Layer (SSL), Secure Hypertext Transfer Protocol (HTTPS), and/or the like. Employing such encryption security protocols, the present invention may encrypt all incoming and/or outgoing communications and may serve as node within a virtual private network (VPN) with a wider communications network. The cryptographic component facilitates the process of "security authorization" whereby access to a resource is inhibited by a security protocol wherein the cryptographic component effects authorized access to the secured resource. In addition, the cryptographic component may provide unique identifiers of content, e.g., employing and MD5 hash to obtain a unique signature for an digital audio file. A cryptographic component may communicate to and/or with other components in a component collection, including itself, and/or facilities of the like. The cryptographic component supports encryption schemes allowing for the secure transmission of information across a communications network to enable the component of the present invention to engage in secure transactions if so desired. The cryptographic component facilitates the secure accessing of resources on the present invention and facilitates the access of secured resources on remote systems; i.e., it may act as a client and/or server of secured resources. Most frequently, the cryptographic component communicates with information servers, operating systems, other program components, and/or the like. The cryptographic component may contain, communicate, generate, obtain, and/or provide program component, system, user, and/or data communications, requests, and/or responses.

The Database of the Present Invention

The database component of the present invention may be embodied in a database and its stored data. The database is a stored program component, which is executed by the CPU; the stored program component portion configuring the CPU to process the stored data. The database may be a conventional, fault tolerant, relational, scalable, secure database such as Oracle or Sybase. Relational databases are an extension of a flat file. Relational databases consist of a series of related tables. The tables are interconnected via a key field. Use of the key field allows the combination of the tables by indexing against the key field; i.e., the key fields act as dimensional pivot points for combining information from various tables. Relationships generally identify links maintained between tables by matching primary keys. Primary keys represent fields that uniquely identify the rows of a table in a relational database. More precisely, they uniquely identify rows of a table on the "one" side of a one-to-many relationship.

Alternatively, the database of the present invention may be implemented using various standard data-structures, such as an array, hash, (linked) list, struct, structured text file (e.g., XML), table, JSON, NOSQL and/or the like. Such data-structures may be stored in memory and/or in (structured) files. In another alternative, an object-oriented database may be used, such as Frontier, ObjectStore, Poet, Zope, and/or the like. Object databases can include a number of object collections that are grouped and/or linked together by common attributes; they may be related to other object collections by some common attributes. Object-oriented databases perform similarly to relational databases with the exception that objects are not just pieces of data but may have other types of functionality encapsulated within a given object. If the database of the present invention is implemented as a data-structure, the use of the database of the present invention may be integrated into another component such as the component of the present invention. Also, the database may be implemented as a mix of data structures, objects, and relational structures. Databases may be consolidated and/or distributed in countless variations through standard data processing techniques. Portions of databases, e.g., tables, may be exported and/or imported and thus decentralized and/or integrated.

In one embodiment, the database component includes several tables. A user table may include fields such as, but not limited to: user_id, ssn, dob, first_name, last_name, age, state, address_firstline, address_secondline, zipcode, devices_list, contact_info, contact_type, alt_contact_info, alt_contact_type, DID, and/or the like to refer to any type of enterable data or selections discussed herein. The user's table may support and/or track multiple Entity accounts. A Client's table may include fields such as, but not limited to: user_id, client_id, client_ip, client_type, client_model, operating_system, os_version, app_installed_flag, and/or the like. An Apps table may include fields such as, but not limited to: app_ID, app_name, app_type, OS_compatibilities_list, version, timestamp, developer_ID, and/or the like.

In one embodiment, user programs may contain various user interface primitives, which may serve to update the platform of the present invention. Also, various accounts may require custom database tables depending upon the environments and the types of clients the system of the present invention may need to serve. It should be noted that any unique fields may be designated as a key field throughout. In an alternative embodiment, these tables have been decentralized into their own databases and their respective database controllers (i.e., individual database controllers for each of the above tables). Employing standard data processing techniques, one may further distribute the databases over several computer systemizations and/or storage devices. Similarly, configurations of the decentralized database controllers may be varied by consolidating and/or distributing the various database components. The system of the present invention may be configured to keep track of various settings, inputs, and parameters via database controllers.

Definitions:

Certain Terms are Used Throughout this Document and are Defined as Follows:

| Term | Description |
| --- | --- |
| Assertion | The data record or file representing the Digital Credential in JSON or JSON-LD format. |
| Composability | Composability is a system design principle that deals with the inter-relationships of components. A highly composable system provides recombinant components that can be selected and assembled in various combinations to satisfy specific user requirements. In information systems, the essential features that make a component composable are that it is self-contained and stateless. |
| Claim | A statement made by one or more entities about a specific Entity. |
| Creator | The thing that created the resource. For example, the key that created a Digital Signature. |
| Credential | A qualification, achievement, personal quality, aspect of an Entity's background such as a name, government ID, payment processor, home address, or university degree, or verifiable statement by an Entity about another Entity. Credentials may be stored in Identity Documents. |
| Credential Aggregator ("Vault") | Software that behaves like an IdP and uses the CTP, however, is not actually a chosen IdP for any Credential Recipients; rather it is a storage area for Issuers to send Credentials for later pick up by the Recipient regardless of their IdP of choice. |
| Credential Consumer | An Entity that requests a Credential for processing. |
| Credential Consumer Tool | An application that can request Credentials using the CTP. How the application consumes a Credential once it has been retrieved is an implementation detail. |
| | Recipient |
| Credential Exchange | A transmission of a Credential from one Entity to another Entity. |
| Credential Processor Tool | Software responsible for creating new Credentials for a particular Identity. It uses the CTP to transmit Credentials to an IdP. |
| Credential Service | A program, such as a Credential storage vault or personal Credential "wallet" that stores and protects access to a Recipient's Credentials. |
| Credentials Transport Protocol (CTP) | A set of messages and protocols for issuing, storing, requesting, and transmitting Credentials. |
| Credential Certification | Credential Certification is about proving the Claims made are actually true. This would like employ probing various attributes including, but not limited to: public key ownership, Entity Identity verification and Credential Verification. |
| Credential Validation | The process that demonstrates the information in a Credential is well-formed. |
| Credential Verification | The process that cryptographically demonstrates the authenticity of a Credential. |
| Decentralized Identifier (DID) | A portable URI-based identifier, also known as a DID, that is associated with an entity. These identifiers are most often used in a credential and are associated with recipients such that the credential itself can be easily ported from one identity provider to another without the need to reissue the credential. An example of a DID is: did:b6922d8e-20df-4939-95cd-f79375979178 |
| Digital Credential | A Digital Credential is an electronic document that 1) contains machine-readable data, 2) expresses Claims made by one person or organization about another, and 3) is cryptographically verifiable. |
| Digital Signature (aka Signature) | A mathematical scheme for demonstrating the authenticity of a digital message. |
| Entity | A thing with distinct and independent existence such as an individual person, organization, or instance of a software program. |
| Identity | A set of information that can be used to identify a particular Entity such as a person, software agent, or organization. An Entity may have multiple identities associated with it. |
| Identity Document | A Web-based document that contains statements about a particular Identity. Identity Documents must be accessible in JSON-LD format and may be accessible in other RDF-compatible formats. |
| Identity Document URL | An Identity Document URL consists of an HTTP or HTTPS scheme and denotes an Identity. For example: https://example.org/identities/manu. |
| Identity Owner | An Entity that is in control of a particular Identity Document. |
| Identity Provider (IdP) | A website providing access to one or more Identity Documents. - An IdP is responsible for managing an Entity's Identity (an Entity is usually a person). It must handle requests to associate newly issued Credentials with an Identity and to retrieve Credentials that have already been associated. It |

| Term | Description |
|---|---|
| | uses the CTP to handle these tasks. How an IdP associates and retrieves Credentials is an implementation detail. |
| Interdependent Credential Collection (IDC) | An IDC is made of up of one or more Digital Credentials that are linked together (Linked Data) using JSON or other format. |
| Issuer | The authoritative Entity responsible for data contained and optionally digitally signed in a Credential. |
| JSON/JSON-LD | JSON is intended to mean a lightweight Linked Data format. It is based on the already successful JSON format and provides a way to help JSON data interoperate at Web-scale. JSON-LD is an ideal data format for programming environments, REST Web services, and unstructured databases. Linked Data empowers people that publish and use information on the Web. It is a way to create a network of standards-based, machine-readable data across Web sites. |
| Linked Data | Linked data is intended to refer to a set of best practices for publishing and connecting structured data on the Web. Key technologies that support Linked Data are URIs (a generic means to identify entities or concepts in the world), HTTP (a simple yet universal mechanism for retrieving resources, or descriptions of resources), and RDF (a generic graph-based data model with which to structure and link data that describes things in the world). Linked data is about using the Web to connect related data that wasn't previously linked, or using the Web to lower the barriers to linking data currently linked using other methods. More specifically, Wikipedia defines Linked Data as "a term used to describe a recommended best practice for exposing, sharing, and connecting pieces of data, information, and knowledge on the Semantic Web using URIs and RDF." |
| Resource Description Framework ("RDF") | RDF is one of the key ingredients of Linked Data, and provides a generic graph-based data model for describing things, including their relationships with other things. RDF data can be written down in a number of different ways, known as serializations. Examples of RDF serializations include RDF/XML, Notation-3 (N3), Turtle, N-Triples, RDFa, and RDF/JSON. |
| Recipient | An Entity that is in control of a particular Credential. Typically a Recipient is also the primary topic of the information in a Credential and is the Entity that initiates the transmission of the Credential. Examples: college Recipient, plumber, CPA, job trainee, competitive fisherman, golfer, publisher, commercial driver, insurance policy owner, or the like. |
| User Agent | A program, such as a browser or other Web client that mediates the communication between Recipients, Issuers and Credential Consumers. |
| Uniform Resource Identifier (URI) | In computing, a Uniform Resource Identifier (URI) is a string of characters used to identify a name of a resource. Such identification enables interaction with representations of the resource over a network, typically the World Wide Web, using specific protocols. |
| WebDHT | A mechanism that is used to discover the software services, such as an Identity Provider, associated with an Entity. Technically speaking, it is a Web-based decentralized hash-table built on Web architecture principles that is used to map cryptographic hashes to decentralized identifiers and decentralized identifiers to decentralized identifier documents. The technology is used to map cryptographic hashes of email addresses and passphrases to decentralized identifier documents which can then be used to discover an Entity's Identity Provider. The technology is one way of solving the NASCAR service bootstrap problem. |

The present invention comprises a system and methods for interdependent Identity based Credential collection validation. The system is comprised of a number of different components, potentially operated by different providers. In one embodiment, the system is partially comprised of a Credential Aggregator. Issuers may use a $3^{rd}$-party Credential Aggregator, which acts as a centralized storage system for issued Digital Credentials. This Credential Aggregator will interface with the Issuers of various Credentials. In some embodiments, the Credential Aggregator will provide the organization of a number of predetermined Credentials represented as an IDC. A Credential Consumer will evaluate a given IDC, verifying that each Digital Credential contained in the IDC is valid. If just one of the Credentials in the IDC is invalid, the Credential Consumer would consider the IDC to be invalid.

For example, a person may want to certify that she is a validly licensed patent attorney. To prove this, she will have to prove: (1) her technical background, (2) her graduation from a law school, (3) that she has passed the bar examination in at least one state, (4) that she has passed the patent bar examination, (5) that she is a member in good standing with the State in which she is licensed to practice law, and (6) that she is in good standing with the United States Patent and Trademark Office. Thus, a person who wishes to have her status as a patent attorney verified by a Credential Consumer will have to get 6 Credentials from the Credentials Aggregator. Under the present invention, this person would have to receive a Digital Credential from each respective authoritative Issuer representing each of the 6 requirements.

Here, these Credentials would be sent by a number of Issuers; the State Board of Bar Examiners would be able to provide the Digital Credentials regarding the license to practice law in that given state, as well as whether that person was still a member in good standing; the United States Patent and Trademark Office would provide the Digital Credentials that the person has passed the appropriate examination and is still a member in good standing and potentially proof of the person's technical background as well. However, the Digital Credentials showing this person's technical background is preferably provided by the institution that provided the individual's technical education. In this example, this institution qualifies as a Primary Source Provider. Also, the law school that the person attended would preferably provide the Digital Credential that the person received a law degree from that law school, but the State Board of Bar Examiners would also be able to provide this Digital Credential.

For illustrative purposes only, the system where the preferred embodiment of the present invention would be executed would offer the following scenario for a nurse practitioner (the Recipient in this illustration): The nurse practitioner has just been notified by the state licensing board that her nursing license has been issued to nurse practitioner's DID, represented as a Digital Credential. The nurse practitioner logs into her IdP, such as TrueCred™ Folio, to claim their nursing license Digital Credential. The same procedure repeats for the nurse practitioner's malpractice insurance provider, background check provider and the drug prescription licensing board, all of which issue separate Digital Credentials. All four (4) Credentials are required Claims for nurse practitioner to be in compliance. The IdP provides the means for the Recipient to share her claimed Digital Credentials with Credential Consumers, such as a hospital's compliance officer. Each of the nurse's Digital Credential's meta-data may be independently verified by the Credential Consumer. This typically includes verifying the Issuer, Recipient, and Claims (i.e., short-title, description, criteria, expiration date).

The present invention provides the mean to assemble one or more Digital Credentials into an IDC. Each IDC is represented by a Uniform Resource Identifier (URI). The IDC's URI is supplied to an IDC Credential verifier, which determines the status of the IDC, which is valid or invalid.

The system of the present invention will provide a number of benefits to a user. In a preferred embodiment, entities will be able to form IDCs as specialized Assertions, which allows for simultaneous verification of a set of Digital Credentials. The IDC Assertions are digitally signed to ensure that they cannot be tampered with. The IDC Assertion must be allowed to be verifiable via an independent $3^{rd}$ party. Further, the system of the present invention will be able to add its own arbitrary data to the Assertion and digitally countersign the Issuer's Assertion. In another embodiment an IDC Credential verifier will be able to perform queries on the system of the present invention over the Web using current best practices and common protocols. In a preferred embodiment, the system of the present invention can be scaled to a myriad of Issuers, Recipients, and requests per second In various embodiments, security can be achieved from Public/Private Key Cryptography, a decentralized technology that enables encryption and Digital Signatures to be applied to data. Digital Signatures are designed to be independently verifiable by 3rd parties using software based on open standards.

In yet another embodiment, the system and method of the present invention will provide for: an Issuer. Recipient or Consumer being able to sign up for the purposes of creating or managing IDCs;

The system of the present invention implements as software-as-a-service (SaaS). The SaaS of the present invention validates Digital Credentials in five steps; (1) meta-data associated with a Credential is linked to an DID; (2) This Credential's Assertion is formatted as JSON-LD; (3) the Assertion is signed with a private key; (4) the signed Digital Credential is curated with an IdP; and (5) the Credential meta-data is verified with a public key. All of this functionality is packaged into an API that will be made widely available. In another embodiment the Assertion may be formatted in BSON, TOML, YAML or another data interchange format.

In a preferred embodiment, the present invention is capable of verifying super sets, known as an IDC. That is, there may exist Credential sets that are comprised of another Credentials set, plus at least one additional Credential. In this situation, the present invention may validate and verify all Credentials individually, or may use the verification of the subset as satisfaction of the Credentials contained therein.

In alternative embodiments, entities may endorse ("counter-sign") preexisting Credential sets as satisfying some standard of their own. For example, suppose State A and State B have the same Credentials requirements for driving in either state. State A has already created a Credentials set within the system of the present invention. Accordingly, State B may counter-sign this preexisting IDC and allow State A's licensed vehicle operators to have a verified IDC allowing them to drive within State B.

In some embodiments of the present invention, an IDC may not be modified without compromising the validation of the set. In other embodiments, an IDC may be modified without compromising the verification of the set.

FIG. 1 shows a decision tree of the method of an embodiment of the present invention. As shown here, the interdependencies of the Digital Credentials become highlighted. In this example the method of the present invention is attempting to parse a Recipient's Credentials to determine whether he may validly drive a car. Here, the ability to drive a car (legally) is the IDC ("set"), comprised of Digital Credentials of whether the Recipient has a valid driver's license, and whether the Recipient has a compliant insurance policy with the state upon which he bases his legal right to drive. Digital Credential 101 shows the Recipient's insurance, and Digital Credential 102 shows the Recipient's driver's license. Here, the Recipient's insurance is not valid, so the method returns an invalid status and the set is not fulfilled.

Figure 2:
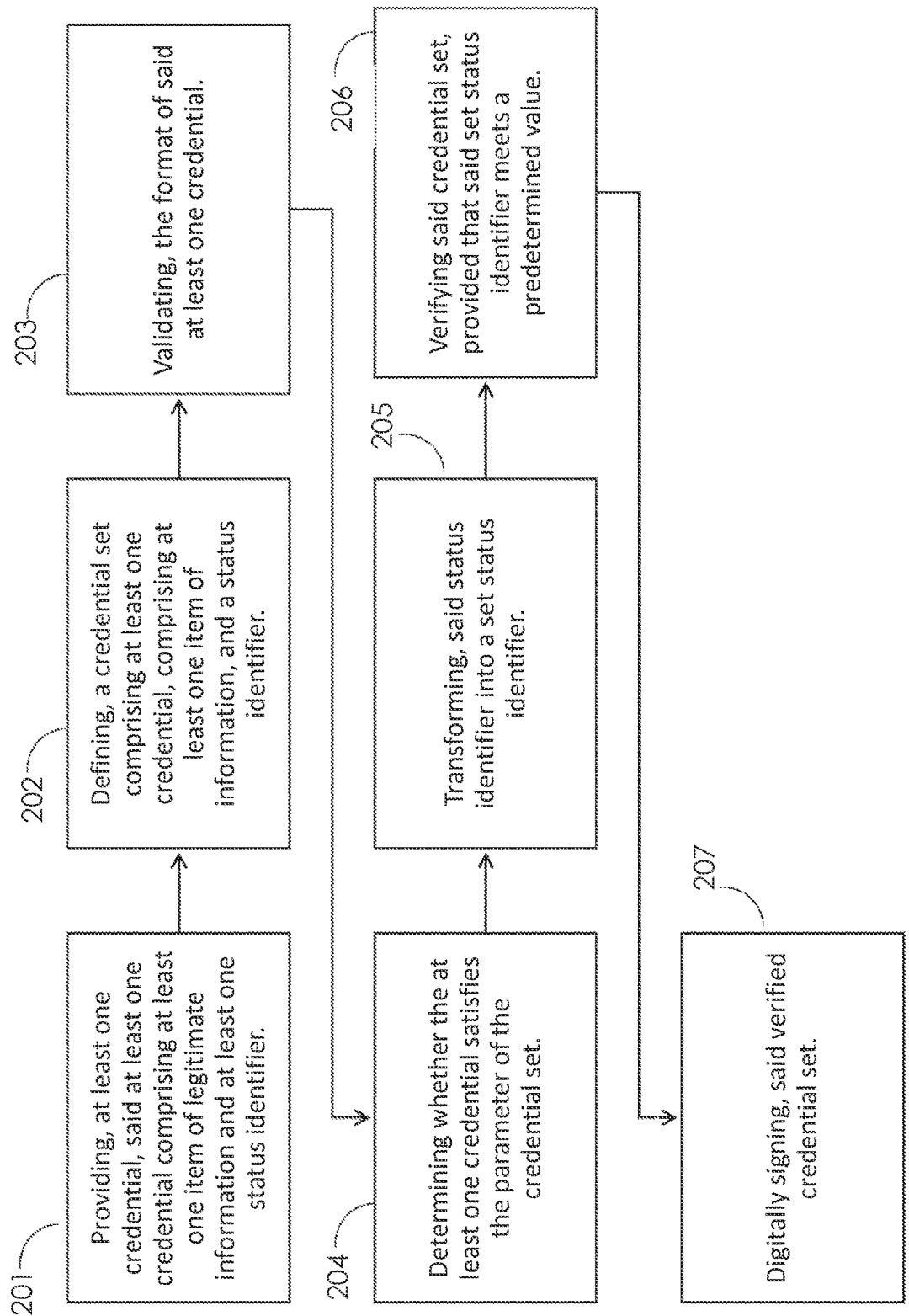
FIG. 2 shows a flow chart illustrating an embodiment of the method of the present invention.

FIG. 2 shows a flow chart illustrating an embodiment of the method of the present invention. In step 201, at least one Digital Credential is provided. Here, a Digital Credential is comprised of at least one item of legitimate information, and at least one status identifier. In a preferred embodiment, this at least one item of legitimate information is provided by a Primary Source Provider, however, in alternative embodiments this information can be provided by an Issuer. By legitimate it is intended to mean that the item of information is a true and accurate representation of what it is intended to represent. The status identifier is used to instruct the system as to whether the Digital Credential may be used to satisfy an IDC. In step 202, an IDC is defined. Preferably this IDC will be comprised of at least one Digital Credential, although it may be comprised of a second Credentials set and at least one additional Digital Credential. It should be noted that the Credential set itself has its own status identifier indicating whether the IDC is ready to be verified. In step 203, the format of the at least one Digital Credential that was provided is validated. This is to ensure that the Digital Credential is in a format that may be accessed by the present invention. In step 204, the present invention determines whether the provided Digital Credential(s) are ready to fulfill a parameter of the IDC; that is, whether the Digital Credential is still good in the eyes of the Issuer and/or Primary Source Provider. If the Digital Credential is still good, then its status identifier is changed accordingly in step 205. In step 206, the IDC is verified if all of its component Digital Credentials have their status identifiers set such that the IDC status identifier is satisfied. Upon the successful completion of step 206, the method proceeds to step 207 where the present invention digitally signs the verified IDC. In another embodiment of the present invention, the verified Credential set does not have to be digitally signed (Step 207).

In another embodiment, the present invention may be used on or facilitated through various devices such as laptops, tablets or smartphones. In this embodiment, such devices may be configured to transmit or broadcast a signal, via Bluetooth Low Energy or similar wireless personal area network technology, of an Entity's location, proximity to a location and the Entity's credential status as validated or verified. Accordingly, the present invention would enable the device to act as a beacon or transponder such that the correct Entity using the device may be securely located and tracked. In this alternative embodiment, an Entity's identification and credentials may be confirmed through their device and thus allowed access to a specific location. For example, a hospital may utilize this embodiment when allowing access to their facility. A hospital may be able to track the movement of an individual through their device but also have credential confirmation that the individual is who they are purporting to be. In yet another embodiment of the present invention, the identification and credentials of an airplane or shipping vehicle may be tracked and confirmed in the air, in route or at all times.

Although this invention has been described with a certain degree of particularity, it is to be understood that the present disclosure has been made only by way of illustration and that numerous changes in the details of construction and arrangement of parts may be resorted to without departing from the spirit and the scope of the invention.

Various other components may be included and called upon for providing for aspects of the teachings herein. For example, additional materials, combinations of materials and/or omission of materials may be used to provide for added embodiments that are within the scope of the teachings herein. In the present application a variety of variables are described, including but not limited to components and conditions. It is to be understood that any combination of any of these variables can define an embodiment of the disclosure. Other combinations of articles, components, conditions, and/or methods can also be specifically selected from among variables listed herein to define other embodiments, as would be apparent to those of ordinary skill in the art.

When introducing elements of the present disclosure or the embodiment(s) thereof, the articles "a," "an," and "the" are intended to mean that there are one or more of the elements. Similarly, the adjective "another," when used to introduce an element, is intended to mean one or more elements. The terms "including" and "having" are intended to be inclusive such that there may be additional elements other than the listed elements.

While the disclosure refers to exemplary embodiments, it will be understood by those skilled in the art that various changes may be made and equivalents may be substituted for elements thereof without departing from the scope of the disclosure. In addition, many modifications will be appreciated by those skilled in the art to adapt a particular instrument, situation or material to the teachings of the disclosure without departing from the spirit thereof. Therefore, it is intended that the disclosure not be limited to the particular embodiments disclosed.

What is claimed is:

1. A system for verifying and digitally signing an interdependent credential collection wherein credentials in the interdependent credential collection are digitally signed by a primary source provider or credential issuer, the system comprising:
   one or more physical processors;
   one or more computer memories; and
   a storage device configured to store one or more computer-executable instructions that, when executed by the one or more physical processors, configure the one or more physical processors to:
   define a first interdependent credential collection comprising a first plurality of digital credentials linked together in the one or more computer memories via a linked data format and having a first interdependent credential collection status identifier indicating a status of the first interdependent credential collection;
      wherein if all of the first plurality of digital credentials are validated and verified, the first interdependent credential collection status identifier is set to a verified state and if at least one of the first plurality of digital credentials is not validated and verified, the first interdependent credential collection status identifier is set to an unverified state;
      wherein each individual digital credential of the first plurality of digital credentials is cryptographically verifiable and comprises machine-readable data, at least one item of legitimate information provided by a primary source provider or issuer expressing a claim made by one person or organization about another, and a digital credential status identifier indicating a status of the individual digital credential determined based on one or more attributes associated with the individual digital credential;
      wherein the status identifier for an individual digital credential indicates whether that individual digital credential may be used to satisfy a parameter of the first interdependent credential collection;
   validate a format of the individual digital credentials of the first plurality of digital credentials to confirm the individual digital credentials are in a format compatible with the first interdependent credential collection;
   determine whether the status identifiers for each of the individual digital credentials of the first plurality of digital credentials satisfy a verification parameter, the verification parameter comprising an indication from the primary source provider or issuer that the individual digital credential is still accurate;
   set the status identifier of each of the individual digital credentials of the first plurality of digital credentials that have been determined to satisfy the verification parameter to verified;
   verify the first interdependent credential collection based on a determination that the status identifiers for each of the individual digital credentials of the first plurality of digital credentials are set to verified;
   set the first interdependent credential collection status identifier to verified; and
   digitally sign the verified first interdependent credential collection.

2. The system of claim 1, wherein the system further includes a credential aggregator the credential aggregator configured to:
   receive credentials from credential issuers;
   store received credentials; and
   provide access to credentials in response to a request from a recipient or credential consumer.

3. The system of claim 1, wherein a recipient of at least one digital credential is student and at least one of the digital credentials comprises a credential issued by an educational institution representing an achievement by the student and at least one of the digital credentials comprises a decentralized Identifier for the student.

4. The system of claim 3, and wherein the system is further configured to receive a request, from a job application system, to make one or more of the student's credentials available for validation.

5. The system of claim 1, wherein one or more digital credentials of the first plurality of digital credentials is associated with a decentralized identifier.

6. The system of claim 1, wherein the interdependent credential collection is digitally signed by a first entity and is digitally countersigned by a second entity.

7. The system of claim 1, the interdependent credential collection is represented by a Uniform Resource Identifier (URI).

8. The system of claim 7, where the system is configured to make the URI available to a credential verifier to determine the status of the interdependent credential collection as valid or invalid.

9. The system of claim 1, wherein the interdependent credential collection comprises a digitally signed prescription credential from a prescriber comprising script information, a patient's decentralized Identifier and a prescriber credential associated with the prescriber; and the system is further configured to make the interdependent credential collection available to a pharmacy.

10. The system of claim 9, further configured to receive a request from the pharmacy for the interdependent credential collection to verify the prescriber credential and proof of the patient's Identity.

11. The system of claim 1, wherein the one or more physical processors are further configured to implement a software-as-a-service for validating the individual digital credentials of the first plurality of digital credentials via an API, wherein to validate a first individual digital credential of the first plurality of digital credentials, the one or more physical processors are configured to:
   link metadata associated with the first individual digital credential with a decentralized identifier;
   format an assertion of the first individual digital credential in a data interchange format, wherein the assertion of the first individual digital credential comprises the data record or file representing the individual digital credential;
   digitally sign the assertion of the first individual digital credential with a private key; and
   verify metadata of the first individual digital credential with a public key.

12. A method for verifying and digitally signing an interdependent credential collection by a primary source provider or credential issuer using a system comprising one or more physical processors and one or more computer memories including a storage device configured to store one or more computer-executable instructions that, when executed by the one or more physical processors, configure the one or more physical processors to perform the steps of:
   defining a first interdependent credential collection comprising a first plurality of digital credentials linked together in the one or more computer memories via a linked data format and having a first interdependent credential collection status identifier indicating a status of the first interdependent credential collection;
   wherein if all of the first plurality of digital credentials are validated and verified, the first interdependent credential collection status identifier is set to a verified state and if at least one of the first plurality of digital credentials is not validated and verified, the first interdependent credential collection status identifier is set to an unverified state;
   wherein each individual digital credential of the first plurality of digital credentials is cryptographically verifiable and comprises machine-readable data, at least one item of legitimate information provided by a primary source provider or issuer expressing a claim made by one person or organization about another, and a digital credential status identifier indicating a status of the individual digital credential determined based on one or more attributes associated with the individual digital credential;
   wherein the status identifier for an individual digital credential indicates whether that individual digital credential may be used to satisfy a parameter of the first interdependent credential collection;
   validating a format of the individual digital credentials of the first plurality of digital credentials to confirm the individual digital credentials are in a format compatible with the first interdependent credential collection;
   determining whether the status identifiers for each of the individual digital credentials of the first plurality of digital credentials satisfy a verification parameter, the verification parameter comprising an indication from the primary source provider or issuer that the individual digital credential is still accurate;
   setting the status identifier of each of the individual digital credentials of the first plurality of digital credentials that have been determined to satisfy the verification parameter to verified;
   verifying the first interdependent credential collection based on a determination that the status identifiers for each of the individual digital credentials of the first plurality of digital credentials are set to verified;
   setting the first interdependent credential collection status identifier to verified; and
   digitally signing the verified first interdependent credential collection.

13. The method of claim 12, further comprising providing a credential aggregator for:
   receiving credentials from credential issuers;
   storing received credentials; and
   providing access to credentials in response to a request from a recipient or credential consumer.

14. The method of claim 12, comprising providing at least one digital credential to a student, wherein the at least one digital credential comprises a credential, issued by an educational institution, representing an achievement by the student and at least one of the digital credentials comprises a decentralized Identifier for the student.

15. The method of claim 14, further comprising receiving a request, from a job application system, to make one or more of the student's credentials available for validation; and making the credentials available to the job applicant system.

16. The method of claim 12, comprising associating a decentralized identifier with one or more digital credentials of the first plurality of digital credentials.

17. The method of claim 12, wherein the interdependent credential collection is digitally signed by a first entity and is digitally countersigned by a second entity.

18. The method of claim 12, comprising representing the interdependent credential collection by a Uniform Resource Identifier (URI).

19. The method of claim 18, comprising making the URI available to a credential verifier to determine the status of the interdependent credential collection as valid or invalid.

20. The method of claim 12, wherein the interdependent credential collection comprises a digitally signed prescription credential from a prescriber comprising script information and a patient's decentralized Identifier and a prescriber credential associated with the prescriber; and the method further comprises making the interdependent credential collection available to a pharmacy to validate the prescription credential.

21. The method of claim 20, comprising receiving a request from the pharmacy for the interdependent credential collection and verifying the prescriber credential and proof of the patient's Identity.

22. The method of claim 12, wherein the one or more physical processors are further configured to implement a software-as-a-service for validating the individual digital credentials of the first plurality of digital credentials via an API, wherein to validate a first individual digital credential of the first plurality of digital credentials, the one or more physical processors are configured to perform the steps of:
  linking metadata associated with the first individual digital credential with a decentralized identifier;
  formatting an assertion of the first individual digital credential in a data interchange format, wherein the assertion of the first individual digital credential comprises the data record or file representing the individual digital credential;
  digitally signing the assertion of the first individual digital credential with a private key; and
  verifying metadata of the first individual digital credential with a public key.

23. The method of claim 12, comprising the step of performing credential certification based on credential attributes including one or of public key ownership, entity identity verification and credential verification.

* * * * *